United States Patent [19]

Sanderson et al.

[11] Patent Number: 4,474,974
[45] Date of Patent: Oct. 2, 1984

[54] PROPYLENE OXIDE BY DIRECT OXIDATION IN CHLOROBENZENE AND HALOCARBONS WITH A SILVER CATALYST

[75] Inventors: John R. Sanderson; Stanley B. Cavitt; Edward T. Marquis, all of Austin, Tex.

[73] Assignee: Texaco Inc., White Plains, N.Y.

[21] Appl. No.: 487,800

[22] Filed: Apr. 21, 1983

[51] Int. Cl.$^3$ .......................................... C07D 301/06
[52] U.S. Cl. ...................................................... 549/533
[58] Field of Search .......................................... 549/533

[56] References Cited

U.S. PATENT DOCUMENTS

| | | | |
|---|---|---|---|
| 3,222,382 | 12/1965 | Lanthier | 549/533 |
| 3,238,229 | 3/1966 | Reid | 549/533 |
| 3,674,813 | 7/1972 | Bljumberg et al. | 549/533 |
| 3,957,690 | 5/1976 | Bobolev et al. | 549/533 |
| 4,046,783 | 9/1977 | Cavitt | 549/533 |

FOREIGN PATENT DOCUMENTS

| | | | |
|---|---|---|---|
| 832471 | 1/1970 | Canada | 549/532 |
| 1506303 | 11/1967 | France | 549/533 |

Primary Examiner—Norma S. Milestone
Attorney, Agent, or Firm—Robert A. Kulason; Jack H. Park; David L. Mossman

[57] ABSTRACT

A process for the direct oxidation of propylene in the presence of oxygen, a silver catalyst and chlorobenzene as a solvent is described. Halocarbon co-solvents such as trichlorotrifluoroethane are used to enhance selectivity to the desired propylene oxide. The direct oxidation is preferably run at a temperature between about 150° to 250° C.

3 Claims, No Drawings

PROPYLENE OXIDE BY DIRECT OXIDATION IN CHLOROBENZENE AND HALOCARBONS WITH A SILVER CATALYST

BACKGROUND OF THE INVENTION

1. Field of the Invention

The invention relates to processes for the direct oxidation of propylene over a catalyst and more particularly relates to the direct oxidation of propylene over a silver catalyst in the presence of chlorobenzene and halocarbons.

2. Other Methods in the Field

The production of ethylene oxide from ethylene has long been known. However, there has been a less successful search for a similar process for producing propylene oxide directly from propylene in an economic manner. The same processes which produced ethylene oxide cannot be adapted to the production of propylene oxide.

As a result, a number of different schemes to produce propylene oxide from propylene or to produce an intermediate to propylene oxide from propylene have been proposed. Initially the research effort seemed to be directed to producing an olefin oxide directly from the olefin in the presence or absence of a solvent. U.S. Patent No. 2,649,463 describes the production of a coordination complex created by the reaction of an olefin with a metal halide where the metal is copper, platinum, palladium, iridium, aluminum, zinc, silver, mercury or antimony. This coordination complex is further reacted with oxygen at a high temperature to produce the olefin oxide plus oxygen-containing metal halides. Hawkins, et al. in an article entitled, "Autoxidation of Olefins," in the *Journal of Applied Chemistry*, Vol. 6, 1956, pp. 1–10, describes a process for the production of epoxides directly from olefins and molecular oxygen over magnesium oxide and/or cobalt naphthenate. The direct production of olefin oxides from a mono olefin and a saturated hydrocarbon with oxygen and water, organic acids or olefin oxide in low concentration is described in U.S. Pat. No. 2,780,634.

British Patent No. 1,582,261 describes how propylene may be reacted with oxygen over a dinitrogen tetroxide catalyst in a liquid medium of a chlorinated organic solvent to produce propylene oxide directly. Propylene oxide may also be prepared directly from propylene and oxygen over a catalyst system comprising a palladium cation plus a chloride anion in the presence of a phosphorous or arsenic ligand as revealed in U.S. Pat. No. 4,256,649.

Further, U.S. Pat. No. 2,784,202 outlines how propylene in a liquid hydrocarbon solvent, such as benzene, in the presence of oxygen and water, organic acids or propylene oxide in low concentration yield propylene oxide when heated at a temperature between 130° and 300° C. Propylene oxide is also proposed to be made directly from propylene in benzene in the presence of oxygen over a cobalt, copper, magnesium, vanadium or chromium catalyst where barium or lead is used as a promoter for the catalyst, according to U.S. Pat. No. 3,071,601. Brill, et al. in *Journal of Organic Chemistry*, Vol. 29, 1964, pgs. 140–143, describes a process for passing olefins and oxygen, frequently in contact with or dissolved in benzene over various catalysts such as azobisisobutyronitrile, cadmium oxide, cobaltic acetylacetonate, magnesium oxide or methyl ethyl ketone peroxide to produce various oxidation products, including the desired epoxides. U.S. Pat. No. 3,132,156 reveals that ethylene, propylene or butylene oxide may be produced directly from ethane, propane or butane under very precise conditions. These conditions include a temperature of between 425° to 575° C., an oxygen volume percent of between 4 and 14, a contact time with the oxygen of between 0.07–1.5 seconds, a pressure of between 20 to 150 psig and constant concentrations of reactants. Epoxides may also be produced from olefins and oxygen which are in an inert reaction medium when they are brought in contact with a rhenium catalyst and 0.05 to 15 weight percent of a reaction modifier comprised of an alkyl aryl or cyclo alkyl cyanide, pyridine or quinoline in accordance with the invention described in U.S. Pat. No. 3,316,279.

Other schemes for producing olefin oxides from olefins and oxygen by means of a solvent or liquid reaction medium include the following. U.S. Pat. No. 3,153,058 employs polyacyl esters of polyhydroxy alkanes, polyhydroxy cycloalkanes, polyglycols or mixtures thereof as the solvent. Materials selected from saturated aliphatic, alicyclic and aromatic nitriles and mixtures thereof form the solvent in U.S. Pat. No. 3,210,380. Boric acid esters form the liquid reaction medium in U.S. Pat. No. 3,210,381. U.S. Pat. No. 3,228,967 uses major amounts of acetone as the solvent. Carbonic acid esters are employed in U.S. Pat. No. 3,228,968, and at least 25 percent by weight of certain ketones serves as the reaction medium in U.S. Pat. No. 3,232,957. Halogenated benzenes serve as the solvent in U.S. Pat. No. 3,238,229 while benzoic acid esters are employed in a similar reaction described in U.S. Pat. No. 3,281,433. Olefin oxides may be prepared directly from olefins and oxygen over a hydrocarbon soluble, phosphorous molybdenum-hydroxy compound catalyst according to the disclosure in U.S. Pat. No. 3,856,826. The approach of making epoxides directly has never been commercially feasible because all of the methods explored gave low yields of epoxides.

Other schemes work somewhat differently from those described above. U.S. Pat. No. 4,237,331 reveals that olefins may be reacted with oxygen in the presence of a suitable surfactant and a diluent over a palladium/copper/boric acid catalyst to produce carbonyl compounds. Propylene may be reacted with acetaldehyde and oxygen in the presence of a boron-containing compound which also has a metal from Groups IVB, VB or VIB of the Periodic Table to give propylene oxide and acetic acid, according to the teaching of U.S. Pat. No. 4,256,650. However, the mechanism to the propylene oxide in this method apparently goes through a peracid intermediate which is not present in the mechanism of the present method. U.S. Pat. No. 3,071,601 instructs that propylene may be reacted with oxygen over a cobalt, copper, manganese, vanadium or chromium catalyst with barium or lead as a promoter to give propylene oxide.

French Patent No. 1,386,354 reveals the oxidation of olefins with oxygen in the presence of a solvent partially miscible with water and a cobalt catalyst at elevated temperatures and pressures. Finally, British Patent No. 1,037,946 teaches a method of oxidizing propylene in gas or liquid phase over a silicon-based catalyst such as a silicic ester.

As may be seen above, the use of organic, aromatic solvents, in general, is known for direct oxidations. It is also known in the art to produce olefin oxides, particularly ethylene oxide, by the reaction of the olefin in the vapor phase in the presence of silver catalysts. The direct oxidation of propylene to propylene oxide in the presence of silver catalysts is also known, but the selectivity to the oxide is low (50% at best). The direct liquid phase, noncatalytic oxidation of propylene is also known but again results in low selectivity to the desired oxide and gives a large number of co-products. See Stanford Research Institute Report No. 2C, p. 259).

It is also known to oxidize propylene to propylene oxide in the presence of silica containing oxides of elements such as scandium as taught in German Offenlegungschrifft No. 2,313,023. In this process, acetone is used as a solvent, and under these conditions acetone is consumed along with the propylene.

U.S. Pat. No. 2,985,668 teaches the reaction of unsaturated compounds (including propylene) with oxygen in the liquid phase using high boiling solvents. The catalysts were finely divided silver catalysts suspended in the liquid. The solvents used were mainly high boiling esters of carboxylic acids. However, the inventors herein have found that the yields of propylene oxide were considerably less than those indicated in this patent when dibutyl phthalate is used as the solvent (taught by Example I therein).

Most of the prior art work concerning the silver catalyzed oxidation of olefins has been with ethylene and it is known that additives such as ethylene dichloride and other chlorinated hydrocarbons retard the formation of by-products (U.S. Pat. Nos. 2,279,469 and 2,734,906).

Despite all of the investigative routes described so far and the ones that have been devised which have not been described, there is still a need for an efficient method for making propylene oxide from propylene, in addition to making the alkylene oxides from other olefins, which does not involve a highly corrosive or highly expensive catalyst system.

SUMMARY OF THE INVENTION

The invention concerns a process for the direct oxidation of propylene to propylene oxide by reacting propylene with oxygen in chlorobenzene solvent in the presence of a silver oxide on alumina catalyst or a silver on alumina catalyst, where a halocarbon co-solvent is present which has the structure

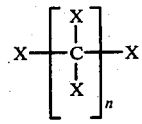

where X are the same or different halogen atoms and n ranges from 2 to 12.

DETAILED DESCRIPTION OF THE PREFERRED EMBODIMENTS

Propylene oxide is generally prepared by reacting oxygen or air with propylene in chlorobenzene (a non-polar, aromatic organic solvent) and one or more halocarbon cosolvents in the presence of a silver or silver oxide on alumina catalyst. The process is particularly advantageous because it can produce propylene oxide directly, in one step. Propylene oxide is of interest in the manufacture of important high volume products, including urethane polyols, alkylene glycols, surfactants and detergents, alkanolamines, fumigants, synthetic lubricants, gasoline additives and elastomers.

Propylene, $CH_2=CH-CH_3$, is the main feedstock. Of course, molecular oxygen in a pure form or air is an essential co-reactant for the method of this invention. When the term "oxygen" is used, either air or pure oxygen is encompassed.

The solvent must be a compound that is inert with respect to the oxidation reaction. These compounds may be generally described as non-polar, aromatic organic solvents. It has been found that chlorobenzene is far and away the best solvent for use in making propylene oxide and thus its use is required herein. The solvent should be present in an amount ranging from 1:50 to 50:1 based on the propylene feed.

The catalyst found useful in the method of this invention is silver or silver oxide on alumina. Other catalyst supports may be used but alumina is preferred. This catalyst can be written as Ag or $Ag_2O$ on $Al_2O_3$. This catalyst is much less corrosive than many of those used in other methods, especially the halide systems. Also, the catalyst levels may range from about 0.50 to 250 wt. % based on the propylene charge.

An important part of the invention is the cosolvent; namely, the halocarbons. As will be shown, the presence of a halocarbon enhances the product selectivity to the desired propylene oxide. Thus, these materials could be called additives or selectivity enhancers as well as cosolvents.

The appropriate halocarbons may be defined by the structure

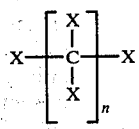

where X represents the same or different halogens and n ranges from 2 to 12. A preferred halocarbon is 1,1,1-trichlorotrifluoroethane. While the presence of only one halocarbon has been shown to be effective, it is expected that a plurality of halocarbons would also be useful.

It is preferred that the halocarbon be present in an amount from 0.05 to 50 wt. % based on the quantity of chlorobenzene solvent present. A preferred co-solvent proportion is 1 to 15 wt. %.

The reaction conditions under which the method of this invention may be conducted include a temperature range of from about 150° to 250° C. The preferred temperature range is from 180° to 240° C. The pressure may be one atmosphere or higher. These conditions are milder than found in many of the prior processes discussed earlier. Surprisingly, no period of inhibition or induction is observed in the method of this invention, even at lower temperatures, unlike some prior art methods which would lengthen the reaction time.

The invention will be further illustrated by the following examples which are not intended to limit the scope of the invention.

EXAMPLES I-V

Procedure

Solvent and catalyst (if any) were charged to the autoclave (which was equipped with a magnedrive stirrer) and the autoclave sealed. A weighed amount of propylene was pressured into the reactor and the contents heated to 200° C. The reactor was then pressured to ~100 psig over autogeneous pressure with oxygen, and repressured every 15–30 minutes. After each addition of oxygen, there was an exotherm. At the end of the reaction, the mixture was cooled to room temperature, the gas vented and the liquid decanted from the solid catalyst. The liquid was analyzed by vapor phase chromatography (VPC) in terms of area percent (A%). These results are useful primarily for comparison with each other. The results are shown in Table I.

in the art could determine an exact combination of solvents, temperature and mode of addition to optimize the yield.

We claim:

1. A process for the direct oxidation of propylene to propylene oxide comprising
   reacting propylene with oxygen in chlorobenzene solvent in the presence of a catalyst selected from the group consisting of silver on alumina or silver oxide on alumina at a temperature between about 150° and 250° C. and where 1,1,1-trichlorofluoroethane is present as a co-solvent in an amount ranging from 0.05 to 50 wt. % based on the chlorobenzene solvent.

2. The process of claim 1 in which the silver caytalyst is present in the proportion ranging from about 0.50 to 250 wt. % based on the quantity of the propylene.

3. The process of claim 1 in which the solvent to propylene weight ratio ranges from about 1:50 to 50:1.

TABLE I

PROPYLENE OXIDE BY DIRECT OXIDATION

| Example | Auto-Clave[1] | Solvent[2] (ml) | Propylene, (g) | Catalyst | g | (% Ag) | Time (Hr) | Temp. (°C.) | PSIG (Total) | No. times Pressured | A % PO |
|---|---|---|---|---|---|---|---|---|---|---|---|
| I | 300ss | Chlorobenzene, 100 Freon-113 (1) | 21 | $Al_2O_3Ag$ | 50 | (9.2) | 4 | 200 | 450 | 8 | 1.5 |
| II | 300ss | Chlorobenzene, 100 Freon-113 (5) | 21 | $Al_2O_3Ag$ | 50 | (9.2) | 3 | 200 | 480 | 8 | 1.7 |
| III | 300ss | Chlorobenzene, 100 Freon-113 (10) | 21 | $Al_2O_3Ag$ | 50 | (9.2) | 3 | 200 | 520 | 7 | 2.0 |
| IV | 300ss | Freon-113, 100 | 21 | $Al_2O_3Ag$ | 50 | (9.2) | 3 | 200 | 650 | 6 | 1.1 |
| V | L-H | Chlorobenzene, 300 | 42 | None | — | — | 3 | 200 | 450 | 7 | 0.59 |

| Example | Products: Area % Selectivity | | | |
|---|---|---|---|---|
| | Carbon Dioxide | Acetaldehyde | Propylene Oxide | Acetone |
| I | 14 | 5 | 49 | 8 |
| II | 17 | 5 | 51 | 9 |
| III | 9 | 8 | 59 | 7 |
| IV | 6 | 2 | 32 | 40 |
| V | 14 | 4 | 13 | 7 |

[1] 300 ss = 300 ml stainless steel autoclave; L-H = one-liter Hastelloy autoclave
[2] Freon-113 = DuPont product trichlorotrifluoroethane.

It may be seen from Table I that the selectivities to propylene oxide for those examples where trichlorotrifluoroethane and chlorobenzene are employed (Examples I–III) are higher than where only the halocarbon is used (Example IV) and especially where no catalyst and only chlorobenzene as solvent is used (Example V).

Many modifications may be made in the method of this invention by those skilled in the art to maximize the yields of the desirable oxides without departing from the spirit and scope of the invention which is defined only by the appended claims. For example, one skilled